United States Patent [19]

Fabo

[11] Patent Number: 5,891,076
[45] Date of Patent: Apr. 6, 1999

[54] HYPERTROPHIC SCAR DRESSING

[75] Inventor: Tomas Fabo, Mölnlycke, Sweden

[73] Assignee: Molnlycke Health Care AB, Gotenburg, Sweden

[21] Appl. No.: 793,823

[22] PCT Filed: Sep. 19, 1995

[86] PCT No.: PCT/SE95/01062

§ 371 Date: Mar. 4, 1997

§ 102(e) Date: Mar. 4, 1997

[87] PCT Pub. No.: WO96/09076

PCT Pub. Date: Mar. 28, 1996

[30] Foreign Application Priority Data

Sep. 20, 1994 [SE] Sweden .................................. 9403148

[51] Int. Cl.[6] ..................................................... A61L 15/14
[52] U.S. Cl. ................................................ 602/52; 602/58
[58] Field of Search ..................................... 424/402, 443, 424/444, 445, 446, 447, 448, 449; 428/604; 604/304, 386; 602/58, 52

[56] References Cited

U.S. PATENT DOCUMENTS

| 4,838,253 | 6/1989 | Brassington et al. | 128/156 |
|---|---|---|---|
| 4,928,681 | 5/1990 | Langston et al. | 128/156 |
| 4,991,574 | 2/1991 | Porknell et al. | 128/156 |
| 5,230,701 | 7/1993 | Meyer et al. | 602/76 |
| 5,635,201 | 6/1997 | Fabo | 424/443 |

FOREIGN PATENT DOCUMENTS

| 0 251 810 | 1/1988 | European Pat. Off. . |
| 0 300 620 | 1/1989 | European Pat. Off. . |
| WO 93/19710 | 10/1993 | WIPO . |

*Primary Examiner*—Lila Feisee
*Assistant Examiner*—Nirmal S. Basi
*Attorney, Agent, or Firm*—Young & Thompson

[57] ABSTRACT

A hypertrophic scar dressing includes silicone-gel on that side of the dressing which lies against the user's skin when worn. A flexible carrier sheet (1) is embodied within the silicone-gel such that the gel forms continuous layers (2, 3) on both sides of the carrier material. The silicone-gel is tacky and skin-adherent and the dressing has a thickness of 0.2–1.5 mm.

19 Claims, 2 Drawing Sheets

HYPERTROPHIC SCAR DRESSING

FIELD OF THE INVENTION

The present invention relates to a dressing and then primarily but not exclusively to a hypertrophic scar dressing, said dressing including silicone gel on that side of the dressing which lies against the wearer's skin in use. Other areas of use are also conceivable, however, such as to cover typical operation scars or to cover particularly sensitive skin.

BACKGROUND OF THE INVENTION

In normal wound-healing or sore-healing processes, the abundant vascular network is regenerated in the wound or the sore during the maturing phase and the collagen fibres collect in large bundles. Sometimes this maturing process fails to occur, so that granulation tissue remains beneath the covering epithelium for a relatively long period of time and may even develop and become enlarged. This is the clinical nature of a hypertrophic scar.

A hypertrophic scar is a raised, red and itching enlargement. The scar may be tender to the touch and to other external pressure and can form on every afflicted part of the body, although it is most prevalent after burn injuries and as a result of wounds across the breastbone and in the shoulder regions.

Hypertrophic scars often remain for a very long time, sometimes until the person concerned dies. In the case of adults, the hypertrophic scar will normally transform to a typical soft and pale scar after a year or so. In addition to itching and being relatively unsightly, hypertrophic scars in the region of joints can also impair joint mobility.

There is at present no quick and effective remedy for hypertrophic scars. The maturing phase can be accelerated in some instances, by injecting glucocorticoid into the scar formations.

It has been discovered in recent years that the regeneration rate of hypertrophic scars can be increased by applying silicone-gel plates to the scars. The mechanism by which the silicone-gel interacts with such scars has not been established, however. A number of products are available commercially for this purpose, for instance such products as Dow Corning Silastic Sheeting (Dow Corning), Cica-Care (Smith & Nephew), Epi-Derm (Biodermis), Nagosil (Nagor), among others. These products have the form of molded silicone-gel plates having a thickness of 2–4 mm. In treating hypertrophic scars, these plates are placed over the scars and are worn for a relatively long period of time, often from three to twelve months, until the scars either have decreased or have regenerated.

The known silicone plates are relatively rigid and after having been placed over the scar have insufficient adhesion force to remain securely in position without some form of assistance. Consequently, it is necessary to secure the plates against the skin with the aid of a securing stocking, bandage, self-adhesive tape or some like means.

This makes the known silicone plates difficult to handle and to feel uncomfortable by the patients concerned. Since the patient needs to wear such plates continuously for a long period of time, due to the fact that scar regeneration is a slow process, optimization of patient comfort is of the greatest concern. A product which is difficult to handle and is felt to be uncomfortable can lower the patient's motivation to undergo the treatment.

OBJECT OF THE INVENTION

An object of the present invention is to provide a hypertrophic scar dressing which is easy to handle, comfortable to wear and which will remain in position after having been applied, and which is also cheaper to manufacture than the aforesaid known dressings.

SUMMARY OF THE INVENTION

In accordance with the invention, this object is achieved with a dressing of the kind defined in the introduction which is characterized in that a flexible sheet of carrier material is enclosed in the silicone-gel such as to form a continuous gel layer on both sides of said carrier material; in that the silicone-gel is tacky and adhesive to skin; and in that the dressing has a thickness of 0.2–1.5 mm. There is thus provided a self-fixating dressing which can be easily applied and which is sufficiently flexible to conform to the contours of that part of the body to which it is secured and is thus comfortable to wear. Because the dressing is thin, it also has a high vapor permeability which further enhances wearer comfort. Furthermore, because the dressing is thin less silicone-gel is used than in the case of the known dressings and the cost of producing the inventive dressing is therefore much lower than the cost of producing the aforesaid known dressings.

According to one preferred embodiment of the invention, the dressing includes a liquid-impermeable top sheet on that side of the dressing which is distal from the wearer's skin in use, and the dressing has a thickness of 0.3–0.6 mm. The carrier material is permeable to liquid and the silicone-gel penetrates through the carrier material so that the layers of silicone-gel on respective sides of said carrier material will be in mutual contact, at least in punctiform contact. The carrier material has a thickness of 0.03–1 mm, preferably 0.05–0.1 mm, and a surface weight of 15–150 $g/m^2$, preferably 25–50 $g/m^2$, and is comprised either of nonwoven material, a knitted or woven textile material or of perforated plastic film. The silicone-gel has a penetration number or index P of 5–20 mm, preferably 7–14 mm, and the cohesion of the gel is greater than the adhesive strength of the gel on skin. The silicone-gel is preferably an addition-curing polydimethyl-siloxane gel. The top sheet is conveniently vapor permeable and is comprised, of a polyurethane film having a thickness of less than 0.1 mm, preferably a thickness of about 0.025 mm. The dressing has a flexibility value H of less than 2.3 mm and the skin adhesion strength or force F1 of the dressing is 0.2–3 N, suitably 0.5–2 N and preferably 0.7–1.5 N. The dressing will suitably have a protective covering on that side thereof which is intended to lie against the wearer's skin in use, this protective covering being removed prior to applying the dressing.

BRIEF DESCRIPTION OF THE DRAWINGS

The invention will now be described with reference to the accompanying drawings, in which.

DETAILED DESCRIPTION OF THE INVENTION

Figure 1:
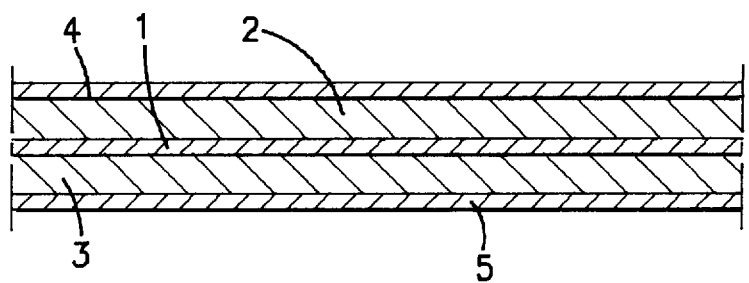
FIG. 1 is a schematic cross-sectional view of one embodiment of an inventive dressing.

The embodiment of an inventive hypertrophic scar dressing illustrated in FIG. 1 is comprised of a sheet of carrier material 1 which is coated on both sides thereof with a respective layer 2, 3 of soft, tacky silicone-gel which is self-adhesive and will adhere to skin. The dressing also includes a top sheet 4.

The silicone-gel contained in the dressing has two purposes.

Firstly, as previously mentioned, the silicone-gel has a medical effect on hypertrophic scars. Secondly, the silicone-gel also functions as a means for securing the dressing to the user's skin and to hold the dressing in place whilst worn. The adhesive strength of the silicone-gel has been adapted to this end, so that the adhesive strength will be sufficiently great to hold the dressing securely in place even when the dressing is subjected to the results of body movements and friction against the skin. However, the adhesive strength shall not be greater than the strength of the bonds with which outer skin cells bind to underlying cell layers. In relation to those adhesive compounds used conventionally in plasters and like devices for holding skin dressings in place, this optimization of the adhesive strength of the silicone-gel affords the advantage that very few skin cells will be stripped-off by the inventive dressing as the dressing is removed. When using conventional plasters or the like of the type Micropore® (3M), Mefix® (Mölnlycke), Hansaplast® (Beiersdorf) or Airstrip® (Smith & Nephew), a layer of dead skin cells will always accompany the adhesive compound each time a dressing is changed, until the stratum corneum is practically eliminated. Since hypertrophic scars require long treatment times with frequent dressing changes, there is a serious danger that the use of conventional adhesive compounds will lead to complications, such as pain among other things. The cohesion in the silicone-gel will preferably be greater than the strength with which the gel adheres to skin, so that the gel will not divide and leave residues on the skin as the dressing is removed.

Tacky, self-adhesive silicone-gels of the kind suitable for use in an inventive dressing are described in GB-A 2 192 142 and EP-A1 0 399 520.

The aforesaid optimization of the adhesive strength of the dressing requires the dressing to be highly flexible and pliable against the surface of the skin on which the dressing is applied. When a dressing is applied to an area of skin which is not flat, such as to a raised hypertrophic scar, stresses and tension will always occur in the dressing due to its flexural resistance. The stiffer the dressing, the greater the residual stresses and tension therein. The skin adhering strength of the dressing according to the described embodiment is adapted so that essentially no skin cells will accompany the dressing as the dressing is removed, and is therewith slighter than the adhesive strength of conventional adhesive compounds. It is therefore important to ensure that after applying the dressing, the residual stresses are small, so as to reduce the risk of the dressing slowly loosening from the skin as a result of these stresses. For this reason, the described dressing is very flexible and pliable, which also enhances user comfort when the dressing is affixed to skin regions that bend or stretch as the body moves. To ensure effective dressing flexibility, the dressing will preferably have a thickness of less than 1.5 mm and preferably a thickness of less than 0.6 mm.

The carrier material 1 functions to reinforce the silicone-gel, which in itself has insufficient cohesion. This reinforcement increases the mechanical strength of the dressing and reduces the danger of the silicone-gel layer separating. For reasons mentioned above, the carrier material shall also be highly flexible and will only increase the stiffness of the composite dressing to a slight extent. The carrier material is comprised of a thin, continuous and coherent material. The carrier material is also preferably permeable to liquid, so that when impregnating the material silicone-gel will penetrate therethrough, at least in a punctiform fashion, so that respective silicone-gel layers 2, 3 on said carrier material will be joined together transversely through said material. The carrier material suitably has a thickness of 0.03–1 mm, preferably 0.1–0.2 mm, and a surface weight of 15–150 g/m$^2$, preferably 25–50 g/m$^2$.

Examples of carrier material are so-called nonwoven, knitted or woven textile material, perforated plastic film and the like.

The primary function of the top sheet 4 is to prevent the dressing from sticking to clothing or other objects that are liable to come into external contact with an applied dressing. The top sheet also contributes towards increasing the wear strength, tensile strength and tear strength of the dressing, and in the majority of cases it is beneficial when the top sheet has a small coefficient of friction against clothing or other materials with which the dressing can be expected to come into contact. The top sheet will preferably also have a high vapor permeability, so that moisture is able to pass from the skin and through the top sheet. The top sheet will also be highly flexible and will suitably comprise a liquid-impervious plastic film, preferably film that has a high vapor permeability. An example of suitable material in this regard is polyurethane having a thickness smaller than 0.1 mm, preferably a thickness of about 0.025 mm. The top sheet is advantageously secured to the gel layer 2 solely by virtue of the intrinsic adhesive force of the gel, so that the total stiffness of the dressing will not be increased or its vapor permeability decreased by the presence of an additional binder layer.

The layers 2, 3 of silicone-gel cover essentially the whole of the two mutually opposing surfaces of the carrier material and all the pores and cavities of the carrier material are filled with silicone-gel in the impregnating process. The combined thickness of the layers 2, 3 will suitably be equal to the thickness of the carrier material, and will preferably be twice as thick. The combined thickness of the two layers 2, 3 is suitably 0.3–0.6 mm. Such thin silicone-gel layers also have a relatively high vapor permeability.

Figure 2:
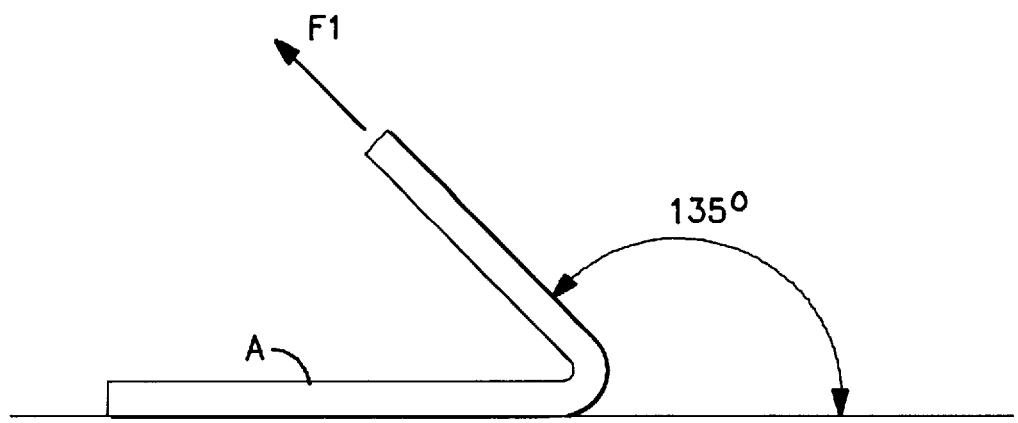
FIG. 2 illustrates schematically a method of determining the adhesiveness of the dressing on skin.

The strength with which the dressing adheres to skin is measured in accordance with a method developed by the inventor, this method being shown schematically in FIG. 2. Dressing strips having a width of 25 mm are applied to the backs of eight subjects and allowed to remain in place for four hours. The strips are then peeled off at a speed of 25 mm/s and the peeling force F1 measured. The strips shall be peeled off such that the angle defined between the lifted part of the strip A and the surface of the skin is 135°, i.e. the obtuse angle shown in FIG. 2. In order to obtain a functional dressing, the force F1 shall have a mean value of 0.2–3 N. It has also been found that an extremely well-functioning dressing is obtained when the force F1 lies within the range of 0.5–2 N, preferably 0.7–1.5 N.

The strength with which the dressing adheres to polished steel plates has also been measured with an 180° peel adhesion test according to ASTM-3330 M-81. In the case of a dressing having a total thickness of 0.45 mm and comprised of a polyurethane film top sheet, thickness 0.025 mm, a polypropylene nonwoven carrier material having a surface weight of 50 g/m$^2$, and a polydimethyl siloxane-gel, the adhesive strength or force F1 against steel was determined as being 0.7 N/25 mm in this test. The steel adhesion strength F1 measured in this way shall lie between 0.3–2.0 N, suitably between 0.5–1.5 N, preferably between 0.7–1.0 N.

Figure 3:
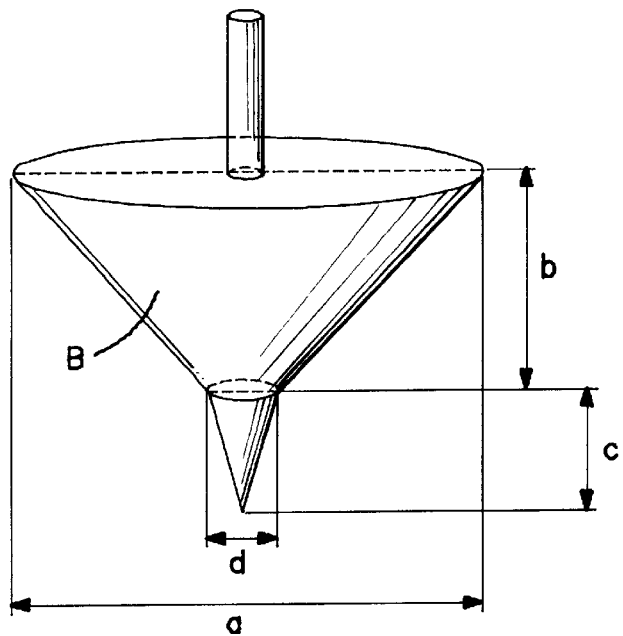
FIG. 3 illustrates a measuring cone for use in a penetration test.
Figure 4:
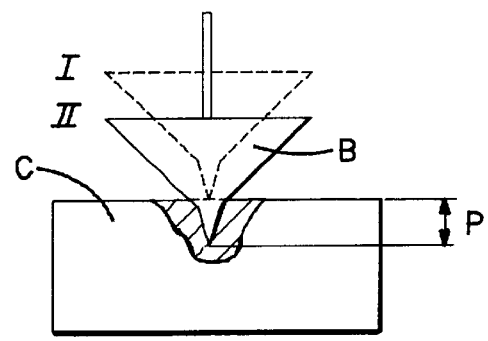
FIG. 4 illustrates schematically a penetration test for measuring softness.

FIGS. 3 and 4 illustrate a method of measuring the softness of a silicone-gel layer, by allowing a cone B weighing 62.5 g to penetrate down into a 30 mm thick silica-gel test body C under the force of gravity. The cone B used is shown in FIG. 3 and has the following measurements: a=65 mm, b=30 mm, c=15 mm and d=8.5 mm. When measuring the softness of the gel, the cone B is first lowered to a position I, shown in broken lines in FIG. 4, in which the cone apex just touches the surface of the gel body C. The cone B is then released so as to enable the cone to penetrate the sample C under the force of gravity. The number of millimeters through which the cone apex has penetrated into the sample body after 5 seconds is determined and the resultant distance constitutes the so-called penetration index P, which will, of course, be greater the softer the sample body.

Silicone-gels having penetration indexes of 5–20 mm, preferably 7–14 mm, have- been found suitable for use in the inventive dressings.

Figure 5:
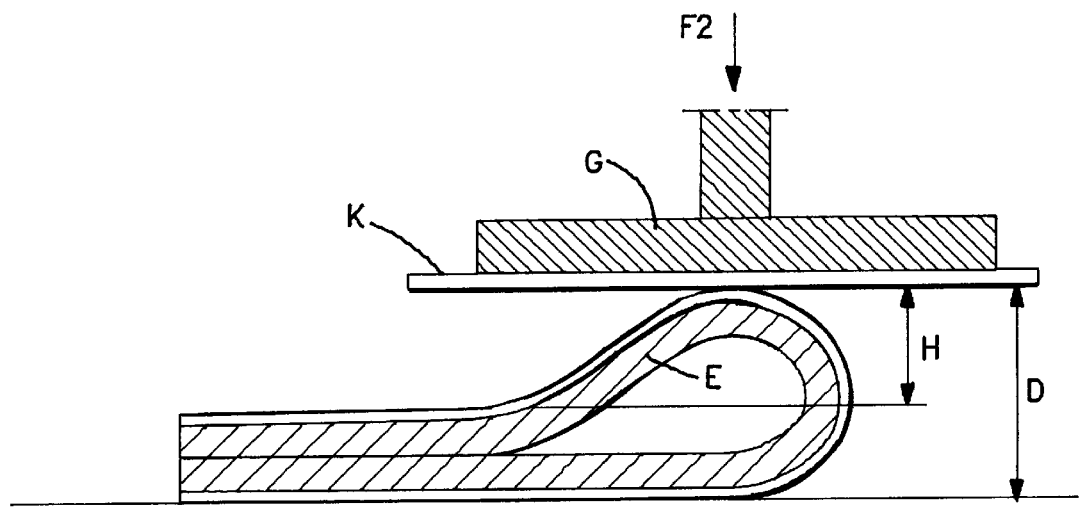
FIG. 5 illustrates schematically a method of measuring the flexibility of a dressing.

The inventor has also developed a method of measuring flexibility, as illustrated in FIG. 5. With this method, the short ends of a strip E measuring 25×100 mm are placed one on top of the other and the strip E is then placed carefully on a flat supportive surface. A loop of greater or smaller size, depending on the stiffness of the strip, will then be located at the end of the folded strip opposite the superimposed short ends thereof. A glide layer K, e.g. a thin paper sheet of well-defined thickness, is then placed on the loop. A plate G is then lowered slowly onto the loop and allowed to burden the loop with a force F2 of 0.15 N. The distance D between the highest part of the loop and the supportive surface is then measured. Twice the thickness of the strip E is then subtracted from the value D, in order to obtain a value H of the flexibility of the tape. The lower the value H, the greater the flexibility of the strip E. An inventive dressing shall have a flexibility value H of less than 2.3 mm, preferably less than 0.7 mm.

The flexibility of an inventive dressing was measured in accordance with the aforedescribed method. The dressing comprised a polyurethane top sheet, thickness 0.025 mm, applied on a soft addition-cured polydimethylsiloxane gel which was reinforced with a polypropylene nonwoven carrier material, thickness 0.15 mm, having a surface weight of 40 g/m$^2$. The dressing had a total thickness of 0.45 mm. The silicone-gel had a penetration number P of 10 mm and the skin adhesive strength F1 was 0.95 N. The flexibility value H was measured with the sample strip folded so as to cause the top sheet to face outwards, and also with the strip folded in the opposite direction, so that the gel layer faced outwards. The flexibility value H was 0 mm in both cases.

The flexibility of Dow Corning Silastic Gel Sheeting® having a thickness of 3.2 mm and including a top sheet was measured in a corresponding manner. With the strip folded so that the top sheet faced outwards, there was obtained a flexibility value H of 7.4 mm, whereas the flexibility value H obtained with the strip folded so that the gel layer faced outwards was 2.4 mm.

The aforedescribed dressing was provided conveniently in manufacture with a protective layer 5 for protecting the free self-adhesive silicone-gel surface of the dressing prior to use. The protective layer 5 may comprise plastic film or a multi-ply material, preferably a liquid impervious material. So as to facilitate removal of the protective layer when wishing to apply the dressing over a hypertrophic scar, the layer may comprise separated protective foils having overlapping edges, similar to the kind used with the majority of conventional plasters.

The described dressing can be sterilized by means of several conventional methods, such as steam sterilization, heat sterilization or sterilization with ethylene oxide.

Because, as earlier mentioned, the inventive dressing is sufficiently adhesive to ensure positive fixation and minimum self-release of the dressing at the same time as the adhesive strength of the dressing is sufficiently low to prevent pain and the removal of skin cells when the dressing is changed, the inventive dressing can also be used in circumstances other than covering hypertrophic scars, even though the dressing is intended primarily for this purpose. For instance, the dressing can be applied effectively to typical surgical scars both before and after removing the stitches, provided that no liquid leaks from the scar. The dressing can also be affixed to particularly sensitive skin, for instance to the skin of babies, to irradiated skin, or to the skin of patients who have been treated with skin-weakening medicaments, such as cortisone, for instance.

It will be understood that the described embodiments of the invention can be modified within the scope thereof. For instance, pharmaceutically active components can be admixed with the silicone-gel, which is particularly suitable vehicle for local anesthetics, for instance xylocaine-type anesthetics, and disinfectants or antibiotics. The top sheet may also be omitted in applications where there is no risk of contact with clothing or the like. It is also possible to use other materials for the top sheet, such as nonwoven, textile or paper materials. The use of liquid-impervious carrier materials is also conceivable when the adhesion of the gel to the carrier material shall be greater than its adhesion to the skin. The invention is therefore only restricted by the content of the following Claims.

I claim:

1. A dressing, which includes silicone-gel on that side of the dressing which, when worn by a user, lies against the user's skin;
    a flexible carrier sheet being enclosed in the silicone-gel so that said gel forms continuous layers on both sides of the carrier material and essentially covers the whole of said both sides, wherein all the pores and cavities of the carrier material are filled with silicone-gel in the impregnating process;
    the silicone-gel being tacky and skin adherent; and
    the dressing having a thickness of 0.2–1.5 mm.

2. The dressing according to claim 1, further comprising a liquid-impervious top sheet on that side of the dressing which-in use, is distal from the wearer's skin.

3. The dressing according to claim 1, wherein the dressing has a thickness of 0.3–0.6 mm.

4. The dressing according to claim 1, wherein the carrier material is liquid permeable and the silicone-gel has penetrated through-the carrier material such as to unite the silicone-gel layers on mutually opposite sides of the carrier material, at least in a punctiform fashion.

5. The dressing according to claim 4, wherein the carrier material has a thickness of 0.03–1 mm, and a surface weight of 15–150 g/m$^2$.

6. The dressing according to claim 5, wherein the carrier material has a thickness of 0.1–0.2 mm and a surface weight of 25–50 g/m$^2$.

7. The dressing according to claim 5, wherein the carrier material is comprised of one of nonwoven material, a knitted or woven textile material, and perforated plastic film.

8. The dressing according to claim 1, wherein the silicone-gel has a penetration number P of 5–20 mm.

9. The dressing according to claim 8, wherein the silicone-gel has a penetration number P of 7–14 mm.

10. The dressing according to claim 8, wherein the cohesion of the gel is greater than the adhesive strength of the gel against skin.

11. The dressing according to claim 8, wherein the silicone-gel is an addition-curing polydimethylsiloxane gel.

12. The dressing according to claim 2, wherein the top sheet is vapor-permeable.

13. The dressing according to claim 12, wherein the, top sheet is comprised of polyurethane film having a thickness of less than 0.1 mm.

14. The dressing according to claim 13, wherein the top sheet has a thickness of about 0.025 mm.

15. The dressing according to claim 1, wherein the dressing has a flexibility value H of less than 2.3 mm.

16. The dressing according to claim 1, wherein the skin adhering strength F1 of the dressing is 0.2–3 N.

17. The dressing according to claim 16, wherein the skin adhering strength is between 0.5–2 N.

18. The dressing according to claim 17, wherein the'skin adhering strength ranges between 0.7–1.5 N.

19. The dressing according to claim 1, further comprising a protective covering on that side of the dressing which is intended to lie against the wearer's skin, the protective covering being removed prior to applying the dressing.

* * * * *